United States Patent
Dreyfuss et al.

(10) Patent No.: US 11,712,233 B2
(45) Date of Patent: Aug. 1, 2023

(54) SOFT SURGICAL CONSTRUCT AND METHOD OF USE FOR TISSUE REPAIR

(71) Applicant: Arthrex, Inc., Naples, FL (US)

(72) Inventors: Peter J. Dreyfuss, Naples, FL (US); Andrew K. Osika, Naples, FL (US); Julia F. Cuny, Naples, FL (US)

(73) Assignee: Arthrex, Inc., Naples, FL (US)

( * ) Notice: Subject to any disclaimer, the term of this patent is extended or adjusted under 35 U.S.C. 154(b) by 349 days.

(21) Appl. No.: 16/891,306

(22) Filed: Jun. 3, 2020

(65) Prior Publication Data

US 2021/0378653 A1  Dec. 9, 2021

(51) Int. Cl.
*A61B 17/04* (2006.01)

(52) U.S. Cl.
CPC .. *A61B 17/0401* (2013.01); *A61B 2017/0403* (2013.01); *A61B 2017/0458* (2013.01); *A61B 2017/0464* (2013.01)

(58) Field of Classification Search
CPC ............ A61F 2/0811; A61F 2002/0841; A61F 2002/0852; A61F 2002/0858; A61F 2002/0882; A61F 2002/0888; A61B 17/0401; A61B 2017/0403; A61B 2017/0414; A61B 2017/042; A61B 2017/0458; A61B 2017/0464; A61B 2017/0496
USPC ........................................................ 606/232
See application file for complete search history.

(56) References Cited

U.S. PATENT DOCUMENTS

| | | | |
|---|---|---|---|
| 7,749,250 B2 | 7/2010 | Stone et al. | |
| 7,905,903 B2 | 3/2011 | Stone et al. | |
| 8,652,172 B2 | 2/2014 | Denham et al. | |
| 9,320,512 B2 | 4/2016 | Dooney, Jr. | |
| 9,788,826 B2 | 10/2017 | McCartney | |
| 9,826,971 B2 | 11/2017 | Lombardo et al. | |
| 9,848,868 B2 | 12/2017 | Saliman | |
| 10,070,856 B1 | 9/2018 | Black et al. | |
| 10,561,410 B2 | 2/2020 | Saliman et al. | |
| 2014/0257382 A1* | 9/2014 | McCartney ........ | A61B 17/0485 606/232 |
| 2015/0164497 A1* | 6/2015 | Callison ............ | A61B 17/0485 606/232 |
| 2015/0173739 A1* | 6/2015 | Rodriguez ....... | A61B 17/06166 606/232 |
| 2017/0071590 A1* | 3/2017 | Macleod ............ | A61B 17/0401 |
| 2019/0231338 A1* | 8/2019 | Michalik ............ | A61B 17/0401 |

OTHER PUBLICATIONS

M. Balke et al., Suture Anchor Refixation of Meniscal Root Tears Without an Additional Portal, Arthroscopy Techniques, vol. 7, No. 5 (May 2018), pp. 511-515.

(Continued)

*Primary Examiner* — Kankindi Rwego
(74) *Attorney, Agent, or Firm* — Blank Rome LLP (57) ABSTRACT

Surgical constructs and methods of use for tissue repair, in which the surgical constructs include a soft fixation device formed of flexible material, the soft fixation device having a head portion formed of a bunching material for anchoring the soft fixation device in a bone tunnel, and a tail portion for pulling the soft fixation device into the bone tunnel. The surgical constructs include one ore repair flexible strands coupled to the head portion of the soft fixation device for engaging tissue to be repaired.

17 Claims, 12 Drawing Sheets

(56) References Cited

OTHER PUBLICATIONS

S. Kuptniratsaikul et al., Arthroscopic Medial Meniscus Root Repair With Soft Suture Anchor without Posterior Portal Technique, Arthroscopy Techniques, vol. 7, No. 5 (May 2018), pp. 453-456.

* cited by examiner

SOFT SURGICAL CONSTRUCT AND METHOD OF USE FOR TISSUE REPAIR

FIELD OF THE INVENTION

The present disclosure generally relates to soft surgical constructs and their use for surgical repair of damaged tissue.

BACKGROUND OF THE INVENTION

When soft tissue, such as a ligament or a tendon, tears or becomes detached from a bone, surgery is usually required to reattach or reconstruct the tissue. A tissue graft may be attached to the bone to facilitate regrowth and permanent attachment. Techniques and devices that have been developed generally involve tying the soft tissue with suture to an anchor, and securing the anchor in a hole provided in the bone tissue.

SUMMARY OF THE INVENTION

The present invention is a surgical construct for tissue repair that comprises a soft fixation device formed of flexible material and that includes a head portion formed of a loop and a tail portion extending from the loop. The head portion is formed of a bunching material for anchoring the soft fixation device in a bone tunnel. The tail portion has a length configured to facilitate pulling the soft fixation device into the bone tunnel. One or more repair flexible strands are coupled to the head portion of the soft fixation device for engaging tissue or tissue graft when repairing damaged tissue.

In certain embodiments, the repair flexible strand extends through and inside of the loop; the loop is closed; the loop and the length of length of the tail portion form one continuous piece; and/or the soft fixation device is formed of a generally tubular sheath.

In other embodiments, the surgical construct further comprises an activation member coupled to the head portion of the soft fixation device for bunching the head portion; the activation member is at least one flexible strand attached to the head portion of the soft fixation device; and/or the activation member extends through the tail portion of the soft fixation device.

In another embodiment, the surgical construct further comprises one or more shuttles associated with the one or more repair flexible strands; and the shuttle is a flexible strand with a length that extends through the tail portion of the soft fixation device.

In some embodiments, each of the repair flexible strands, the activation member, and each of the shuttles is a suture or suture tape; and/or the soft fixation device is formed of a generally tubular sheath.

The present disclosure may yet further provide a method of tissue repair, comprising the steps of pulling a soft fixation device, that has head and tail portions formed of flexible material, into a bone tunnel, tail portion first, by pulling the tail portion of the soft fixation device in an antegrade direction from a proximal open end of the bone tunnel to a distal open end of the bone tunnel; bunching the head portion of the soft fixation device to anchor the soft fixation device in the bone tunnel; and leaving at least one repair flexible strand, that is coupled to the head portion of the soft fixation device, available for engaging tissue when repairing the tissue.

In some embodiments, the step of pulling the soft fixation device into the bone tunnel includes coupling the tail portion to a shuttling device and pulling the shuttling device in the antegrade direction through the bone tunnel; the method further comprises the step of pulling the shuttling device through the bone tunnel in a retrograde direction prior to coupling the tail portion of the soft fixation device to the shuttling device; the step of bunching the head portion of the soft fixation device includes pulling an activation member coupled to the head portion in the antegrade direction; and/or the method further comprises the step of shuttling the at least one repair flexible strand through the bone tunnel in the antegrade direction after the at least one repair flexible strand engages the tissue.

In other embodiments, the step of bunching the head portion of the soft fixation device includes pulling the at least one repair flexible strand in a retrograde direction; the method further comprises the step of tensioning the at least one repair strand to secure the tissue repair; the tissue repair is secured without forming any knots using the at least one repair strand; the method further comprises the step of forming the bone tunnel in an anterior portion of bone; and/or the tissue is a meniscal root.

BRIEF DESCRIPTION OF THE DRAWINGS

FIGS. 3a-3c are elevational cross-section views showing an exemplary method of tissue repair of the present disclosure, using the surgical construct illustrated in FIG. 2a;

FIGS. 5a-5g are elevational views showing another exemplary method of tissue repair of the present disclosure, using the surgical construct illustrated in FIG. 4.

DETAILED DESCRIPTION OF THE PREFERRED EMBODIMENTS

Referring to the figures, the present disclosure relates to surgical constructs and methods of use for repairing tissue. The surgical constructs of the present disclosure are designed for easy anchoring of the same, such as in a tunnel formed or drilled in bone. The design of the surgical constructs of the present disclosure allow for a simplified method of repairing tissue as compared to conventional repair techniques. For example, the need for an inserter device, which is typically used for installing a surgical or anchor construct into a bone tunnel when repairing tissue, is eliminated because the surgical constructs of the present disclosure is pulled into the bone tunnel instead of being inserted or pushed into the bone tunnel, as is conventional. In an exemplary application, the surgical constructs may be used to repair a meniscal root repair by anchoring the same in a transtibial tunnel.

Figure 1A:
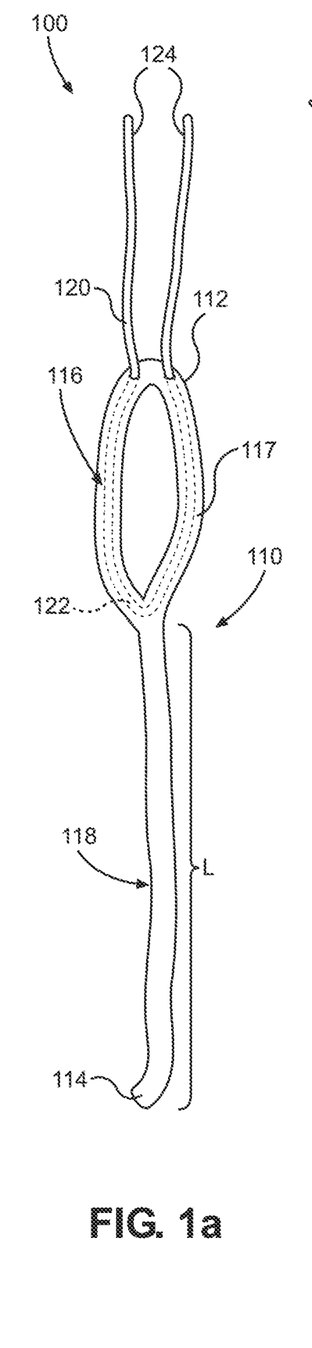
FIGS. 1a and 1b are elevational views of surgical constructs in accordance with exemplary embodiments of the present disclosure.
Figure 1B:
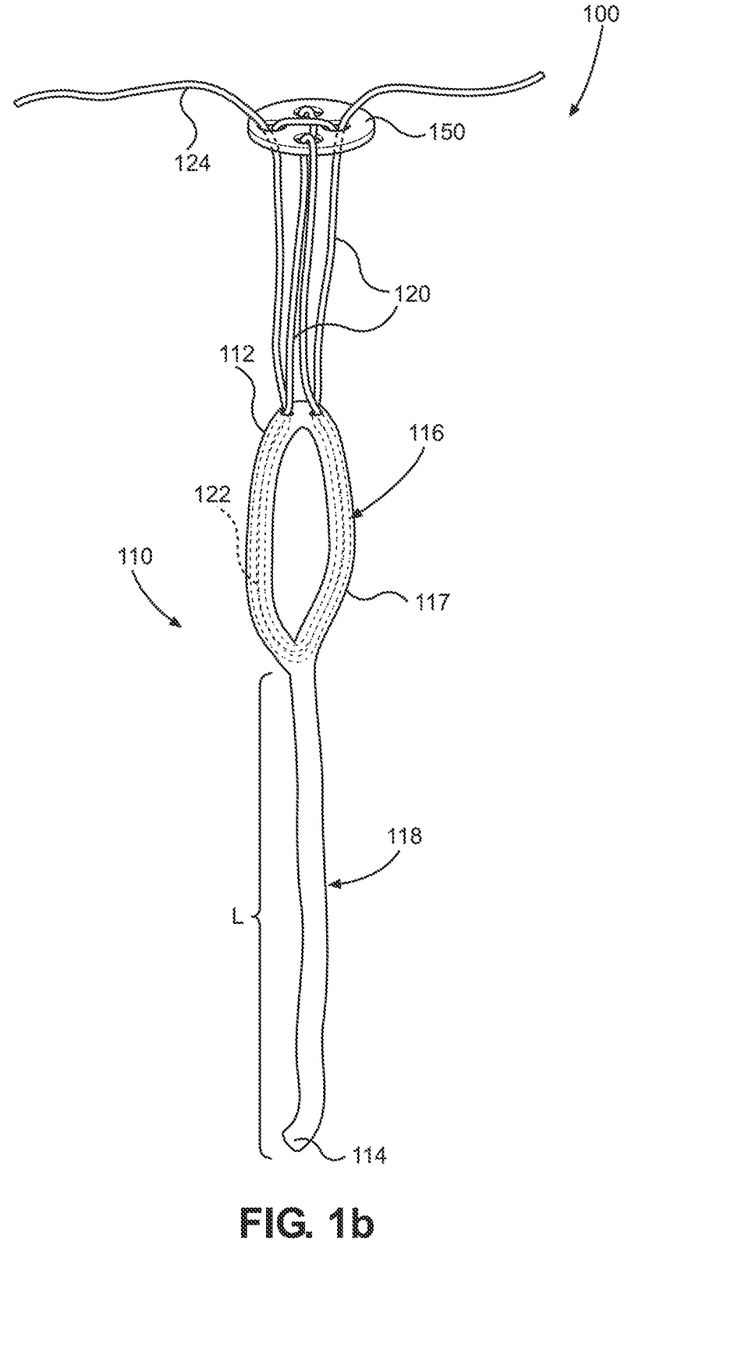

As seen in FIGS. 1a and 1b, in an exemplary embodiment of the present disclosure, a surgical construct 100 generally comprises a fixation device 110 configured for anchoring in a bone tunnel and one or more repair flexible strands 120 coupled thereto for use in repairing damaged tissue. Fixation device 110 may comprise proximal and distal ends 112 and 114, a head portion 116 that ends at the fixation device's proximal end 112, and a tail portion 118 that extends from the head portion 116 and ends at the distal end 114 of the fixation device. Head portion 116 may be formed as a loop 117 that may be continuous and closed, as seen in FIGS. 1a and 1b, or alternatively may be discontinuous or open. Tail portion 118 defines a length L that extends from the loop 117 of the head portion 116. In an embodiment, fixation device 110 is one unitary piece such that the head portion 116 and the tail portion 118 are continuous.

Fixation device 110 is formed of soft or flexible material, preferably suture. Fixation device 110 may be, for example, a sheath, tube or sleeve structure, such as a loosely braided ultrahigh molecular weight polyethylene (UHMWPE) sheath or sleeve, or any similar structure. The sheath or sleeve structure of the fixation device 110 can be provided with open or closed ends, or with at least one open end, or with at least one closed end. The fixation device 110 may also have a tubular shape, partially tubular shape, or may be in the form of a hollow shape construct. The fixation device 110 may be woven or braided structures, or may be formed of yarns, fibers, or filaments or similar materials, or combinations of these materials.

Figure 3A:
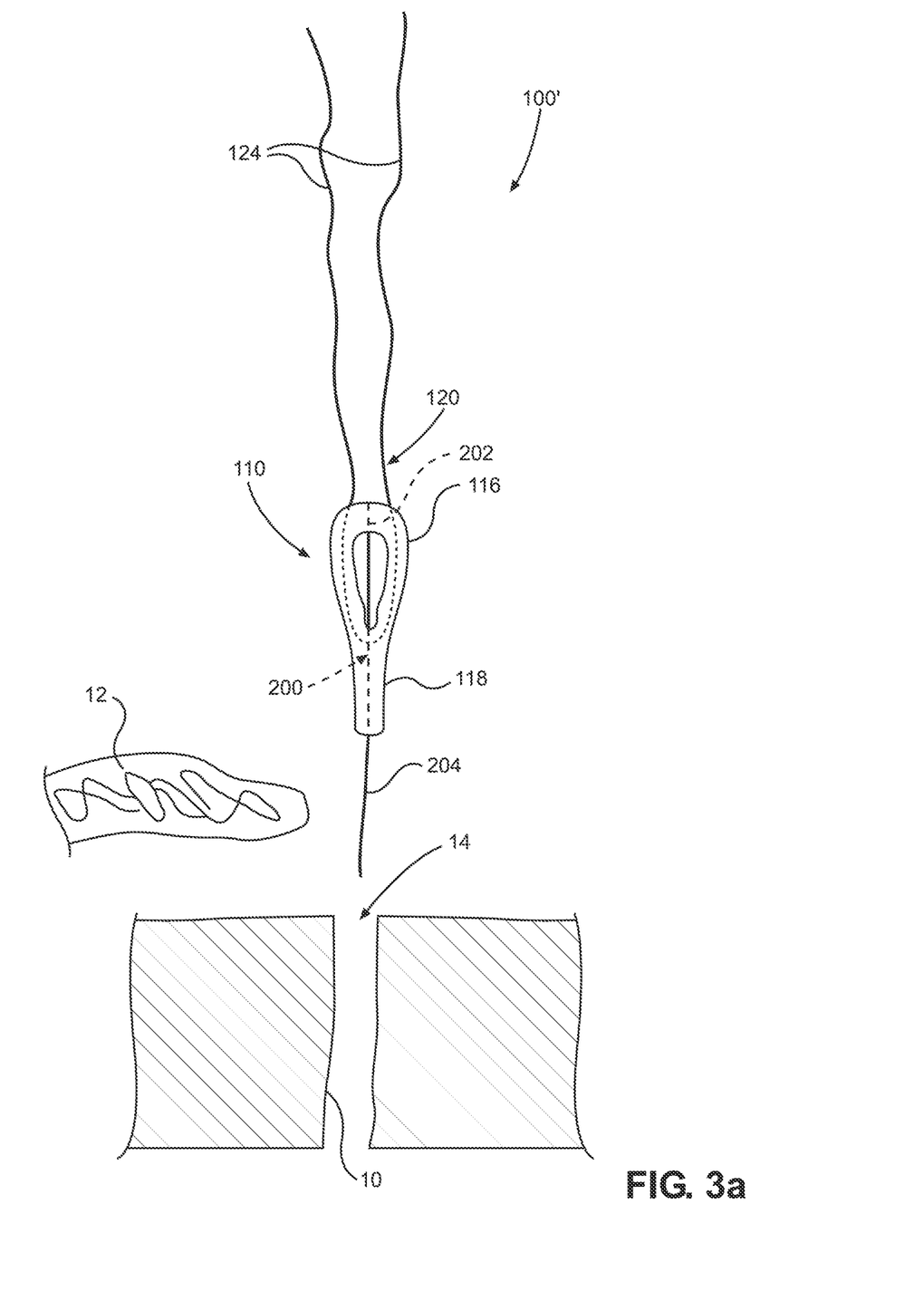

The one or more repair flexible strands 120 are coupled to the head portion 116 of the fixation device 110 such that the repair strand or strands 120 are available for use in repairing the damaged tissue 12 (FIG. 3a). Repair strand or strands 120 can be or can form any known repair construct, knotted or knotless, that is designed for repairing tissue. For example, the repair strand 120 can be a sliding flexible strand, such as a sliding suture or suture tape, with a section 122 of the repair strand 120 extending through and inside of the loop 117 of the fixation device 110, as seen in FIG. 1a. In another example seen in FIG. 1b, sections 122 of more than one repair strand 120 can extend through and inside of the loop 117 of the fixation device 110 and can optionally cooperate with one or more secondary fixation devices 150, such as a button, to form a repair construct, such as a repair construct similar to the Arthrex TightRope® construct, disclosed in commonly owned U.S. Pat. No. 8,439,976, the subject matter of which is incorporated herein by reference. Segments of the one or more repair strands 120 may be outside of the loop 117 such as by weaving in and out of the loop 117. Free ends 124 of the one or more repair strands 120 are available for use in the tissue repair procedure.

The head portion 116 of fixation device 110 and its loop 117 may be formed of any bunching material, that is a material which is configured to be compressed or bunched from an uncompressed position to a compressed position in order to set or anchor the fixation device 110 inside of a bone tunnel, such as bone tunnel 10 (FIG. 3a). Because the one or more repair strands 120 extend through the loop 117 of the fixation device 110, via strand sections 122, the head portion 116 is bunched up in the bone tunnel when tension is applied to the repair sutures 120.

Figure 2A:
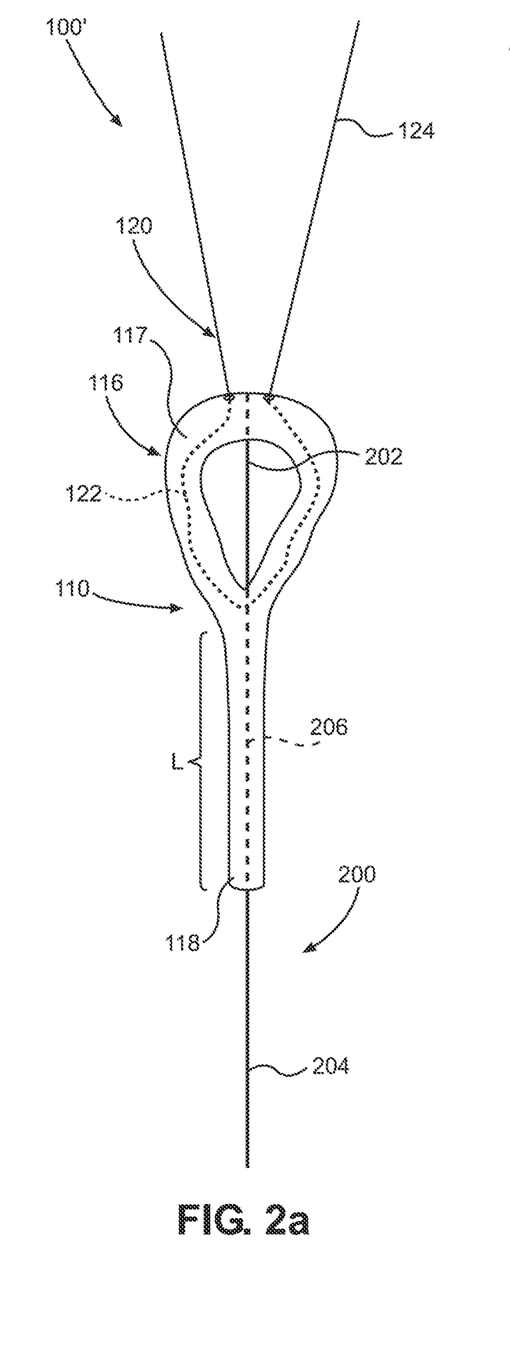
FIGS. 2a and 2b are elevational views of surgical constructs according to other exemplary embodiments of the present disclosure.
Figure 2B:
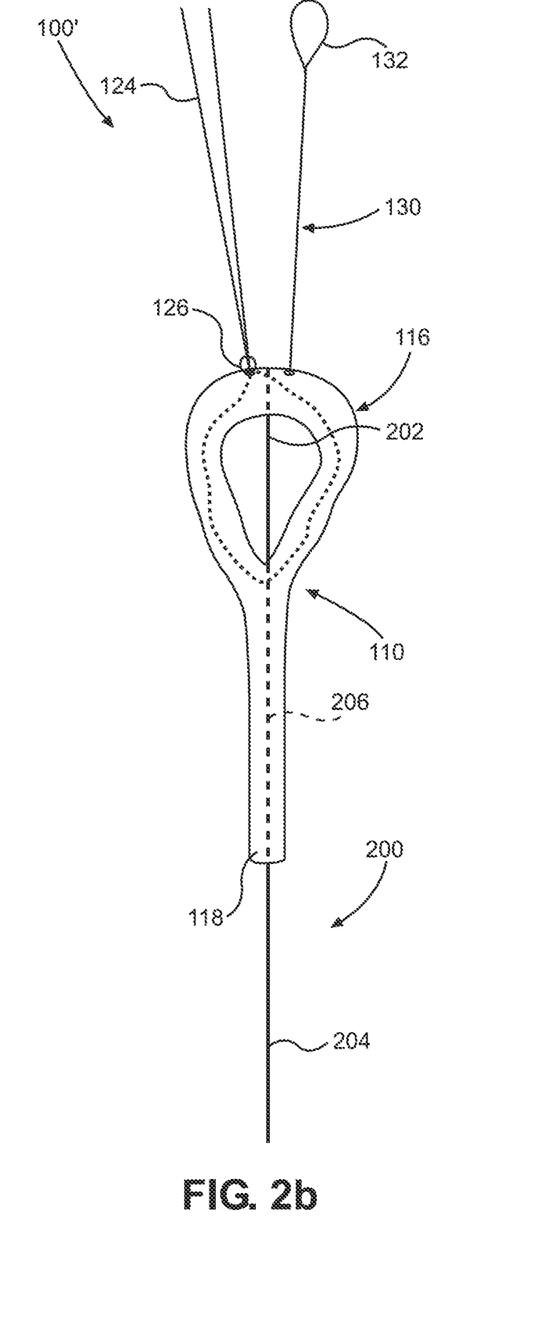
Figure 3B:
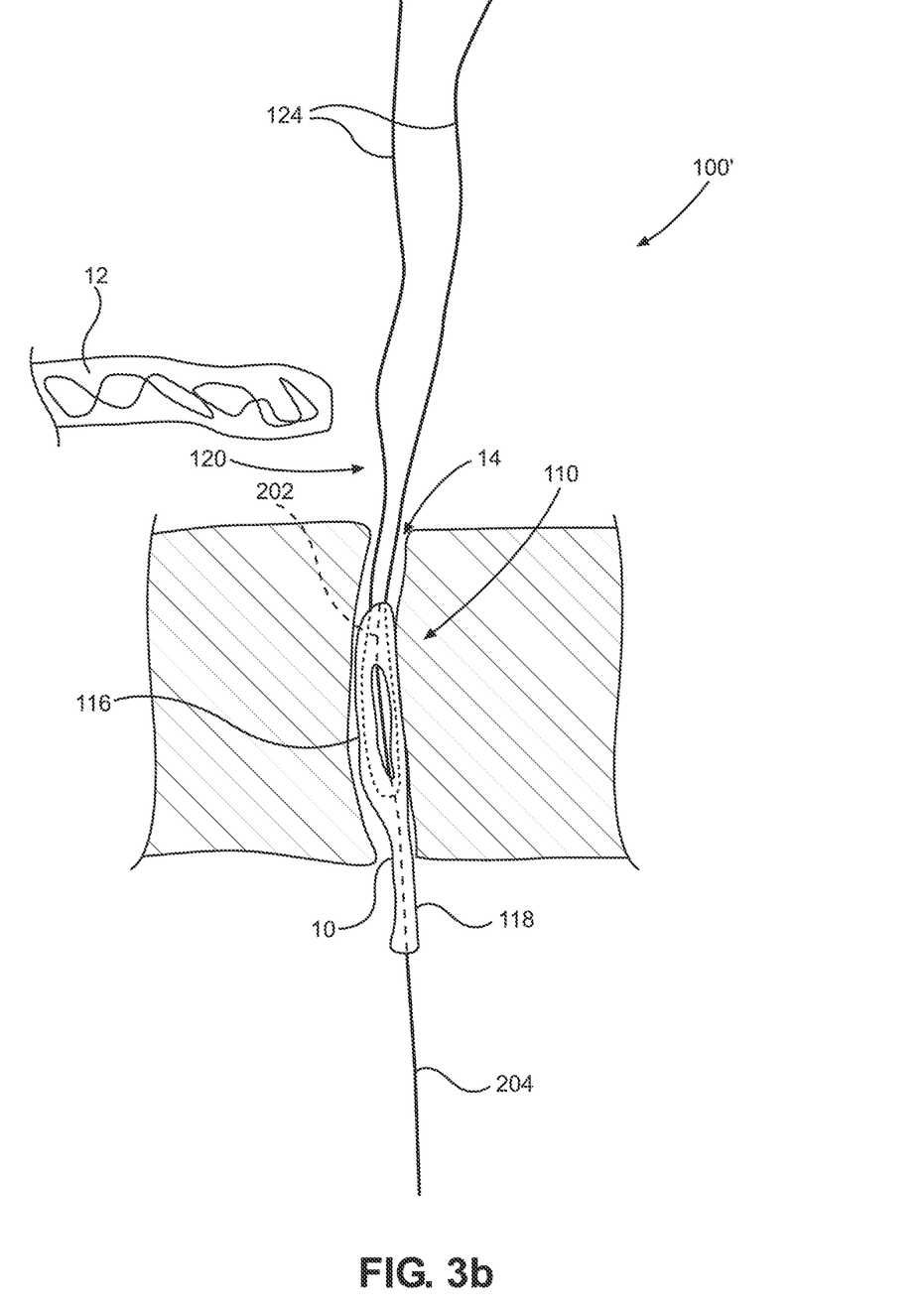
Figure 3C:
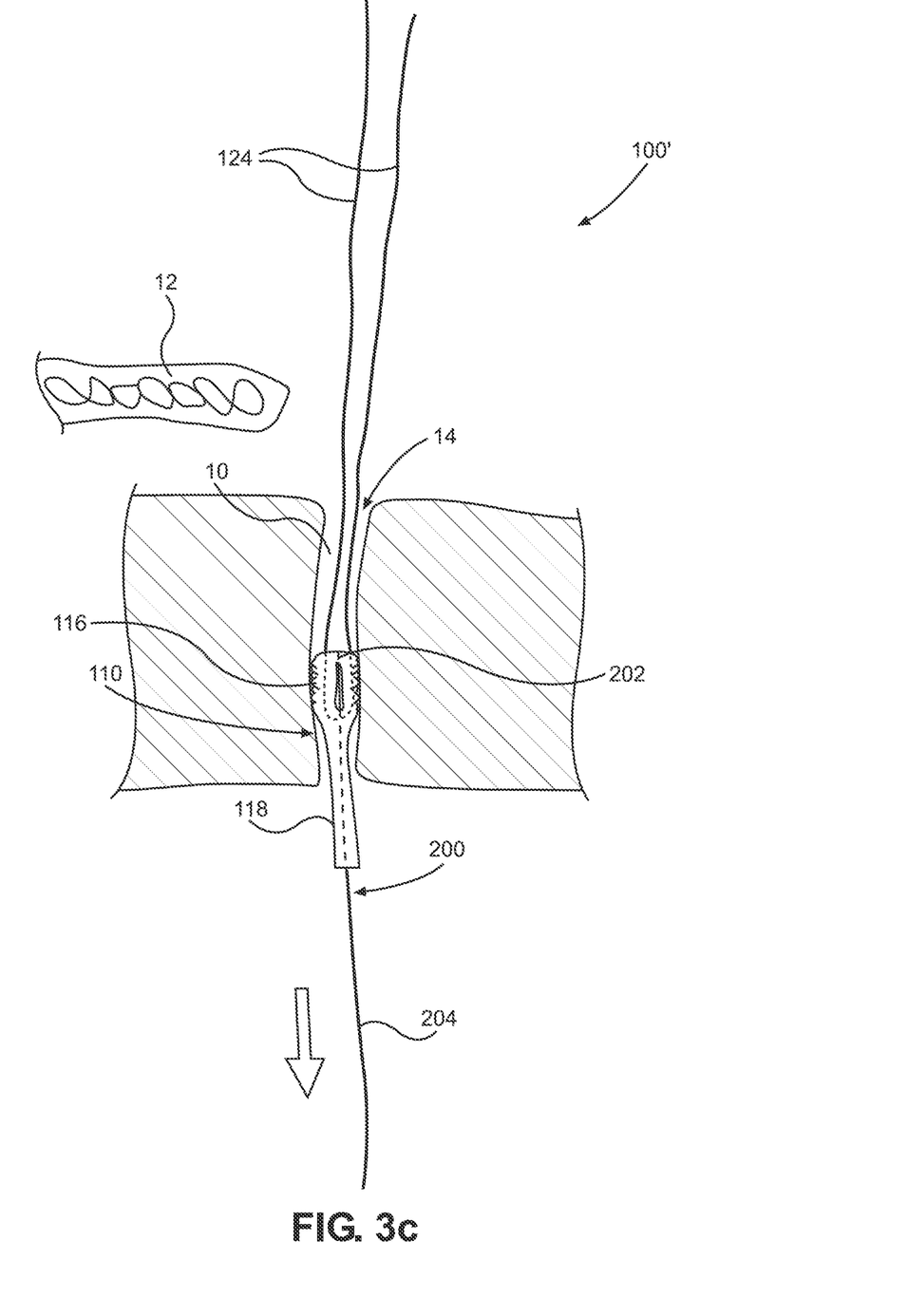

FIGS. 2a and 2b illustrate another exemplary embodiment of a surgical construct 100' that is similar to the surgical construct 100 of the above embodiment and also includes an activation member 200 for bunching of the head portion 116 of the fixation device 110, particularly when anchoring the surgical construct 100' in the bone tunnel 10 (FIGS. 3a-3c).

Activation member 200 may be, for example, a flexible strand, e.g. suture or suture tape, that is coupled to the head portion 116 of the fixation device 110. The activation member 200 may also be more than one flexible strand. The activation member or strand 200 has a coupling end 202 that couples to the loop 117 of the fixation device and an opposite activating distal end 204, which bunches the head portion 116 of the fixation device when tensioned. Coupling end 202 of the activation strand 200 may couple to loop 117 of the fixation device in any coupling manner, such as by threading the end 202 through a section or splice of the loop 117, by cinching the end 202 onto a section of the loop 117 using a fixed loop at the end of the activation strand 200, or by any attachment, e.g. sewing, adhesive, or the like. The activation member or strand 200 has one or more sections 206 that extends through one or more segments of the tail portion 118 of the fixation device 110 with the activating distal end 204 being exposed or outside of the tail portion 118 for easy grasping when bunching the head portion 116 of the fixation device 110. Activating distal end 204 may also be provided with one or more loops to facilitate grasping and pulling of the activation member 200. Or the activation distal ends 204 of two activating strands can be linked or tied together to form a loop for easy grasping.

In the example of the present invention shown in FIG. 2a, the surgical construct 100' is the same as the surgical construct 100 shown in FIG. 1a, except that the activation member or strand 200 is added thereto. In the example shown in FIG. 2b, a shuttle 130 is also provided that is associated with the repair strand 120 for shuttling the repair strand 120 during the tissue repair procedure. The shuttle 130 may have a fixed loop end 132 for receiving the repair strand 120 to shuttle the repair strand, such as through or around tissue (or tissue graft) 12. FIG. 2b also illustrates another example of a repair construct formed by the repair strand 120. In this example, one end 126 of the repair strand 120 may have a fixed loop through which the free end 124 and the length of the repair strand 120 may be threaded to form a self-cinching repair construct. Alternatively, the free end 124 of the repair strand 120 may be threaded through a splice formed in the length of the repair strand 120 to form a cinching repair construct.

FIGS. 3a-3c illustrate an exemplary method of anchoring the surgical constructs of the present disclosure in a bone tunnel, such as bone tunnel 10, for repairing the damaged tissue 14. Although only surgical construct 100' is shown in FIGS. 3a-3c, it will be understood that this method applies to any of the surgical constructs of the present disclosure. Initially, the surgical construct 100' is positioned at or near the pre-drilled bone tunnel 10 such that the tail portion 118 of the fixation device 110 is pointing towards the entrance 14 of the bone tunnel 10. This position of the fixation device 110 allows the fixation device 110 to be pulled into the bone tunnel 10 by the tail portion 118 first in an antegrade direction (downward in the figures). The fixation device 110 is pulled through the bone tunnel 10 by its tail portion 118 using any known shuttling device. The flexible and soft nature of the flexible device 110 allow it to be easily pulled into the bone tunnel 10.

Once the fixation device 110 is pulled into the bone tunnel 10 and properly positioned, the activating distal end 204 of the activation strand 200 is pulled or tensioned to bunch up the head portion 116 of the fixation device 110. The activation strand 200 is pulled in the antegrade direction (shown by the arrow in FIG. 3c) away from the entrance 14 of the bone tunnel 10 to bunch the head portion 116 and anchor the fixation device within the bone tunnel 10, as seen in FIG. 3c. Upon pulling on the activating end 204, the head portion 116 of the fixation device is compressed and bunched because the coupling end 202 of the activation strand 200 is coupled to the head portion 116. The free ends 124 of the repair strand 120 remain outside of the bone tunnel 14 and available for using in repairing the tissue 14.

The fixation device 110 is pulled through the bone tunnel 10 by its tail portion 118 until its head portion 116 is received in the bone tunnel 10, as seen in FIG. 3b. In an embodiment, the head portion 116 is positioned so that it is past, but still generally close to, the entrance 14 of the bone tunnel. That is, the fixation device 110 is pulled by its tail portion 118 via a shuttling device until the head portion 116 thereof is inside of the bone tunnel 10 and relatively close to the entrance 14 of the bone tunnel 10. That leaves the free ends 124 of the repair strand 120 extending outside of the bone tunnel 10 and available for use in the repair of the tissue 12.

Figure 4:
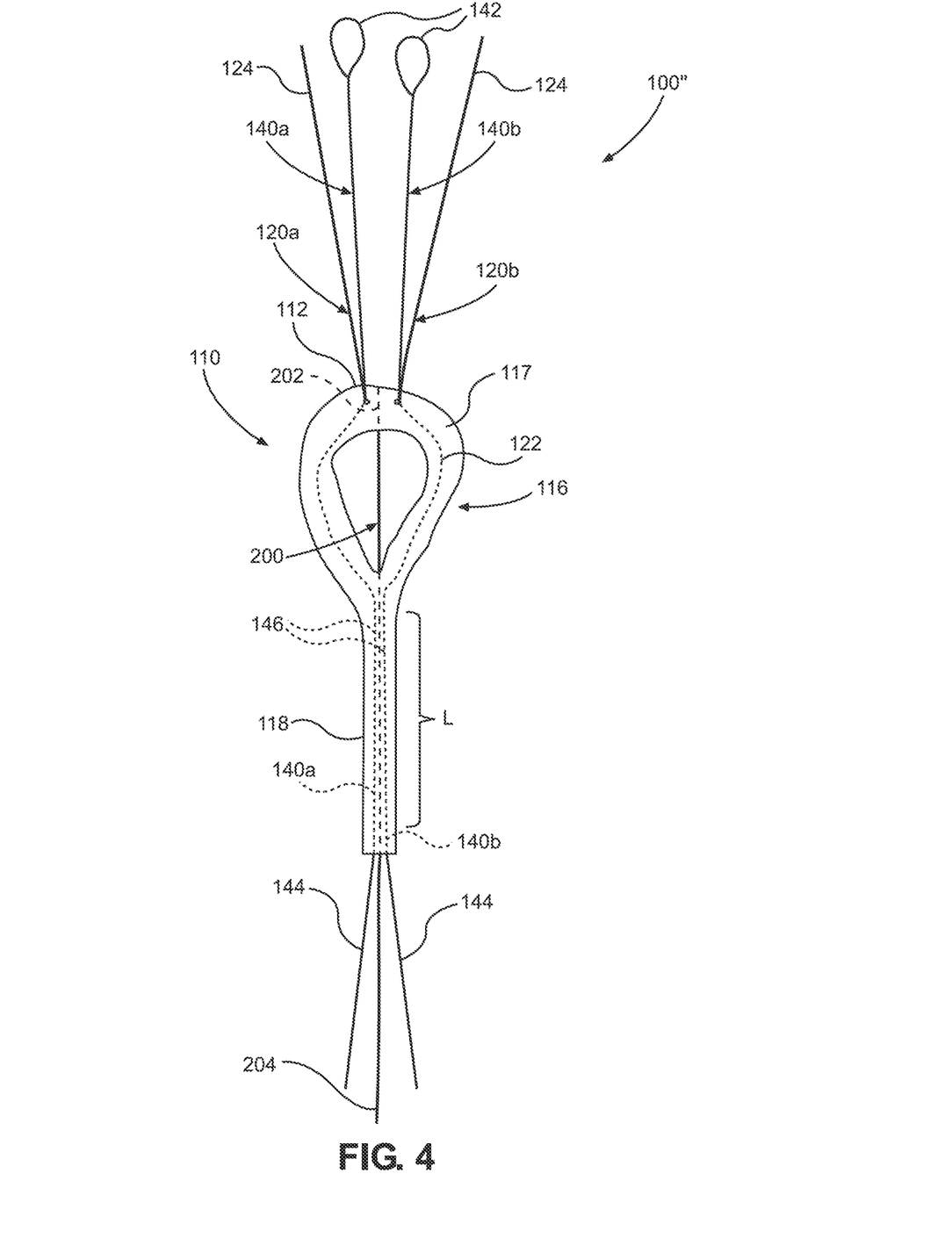
FIG. 4 is an elevational view of another surgical construct according to yet another exemplary embodiment of the present disclosure.

FIG. 4 illustrates yet another exemplary surgical construct 100" of the present disclosure. Surgical construct 100" is similar to the surgical construct 100' above, except that shuttles are provided which extend through the fixation device 110. Like the surgical construct 100' above, surgical construct 100" includes the fixation device 110 with the activation member 200 coupled thereto for applying reverse tension to the surgical construct 100" when anchoring the surgical construct 100" in a bone hole. Similar to the embodiments above, the activation member 200 is coupled to the bunchable head portion 116 of the fixation device 110 by its coupling end 202 and extends through, at least a part of, the tail portion 118 of the fixation device such that its activating end 204 is exposed outside of the fixation device 110. Activation member 200 operates in the same manner to bunch the head portion 116 when anchoring the surgical construct 100" in a bone tunnel.

Surgical construct 100" includes first and second repair flexible strands 120a and 120b that both extend through the loop 117 of the head portion 116 in a manner similar to the repair strands 120 described in the above embodiments. Each repair strand 120a and 120b has an associated shuttle 140a and 140b, respectively, for shutting the repair strands 120a and 120b through the fixation device 110 generally from its proximal end 112 and out through its distal end 114.

Each shuttle 140a and 140b has a fixed loop end 142 and an opposite shuttling end 144. Each fixed loop end 142 is configured to receive the free end 124 of the respective repair strand 120a or 120b. Each shuttling end 144 is configured to extend outside of the fixation device 110 at tail portion 118 to be grasped and pulled for shuttling the respective repair strands 120a or 120b through the fixation device 110. A length 146 of each shuttle 140a and 140b extends through and inside of both the head and tail portions 116 and 118 of the fixation device 110. Segments of the length 146 of each shuttles 140a and 140b can be outside of fixation device 110 by, for example, weaving in and out of the portions 116 and 118 of the fixation device 110.

Figure 5A:
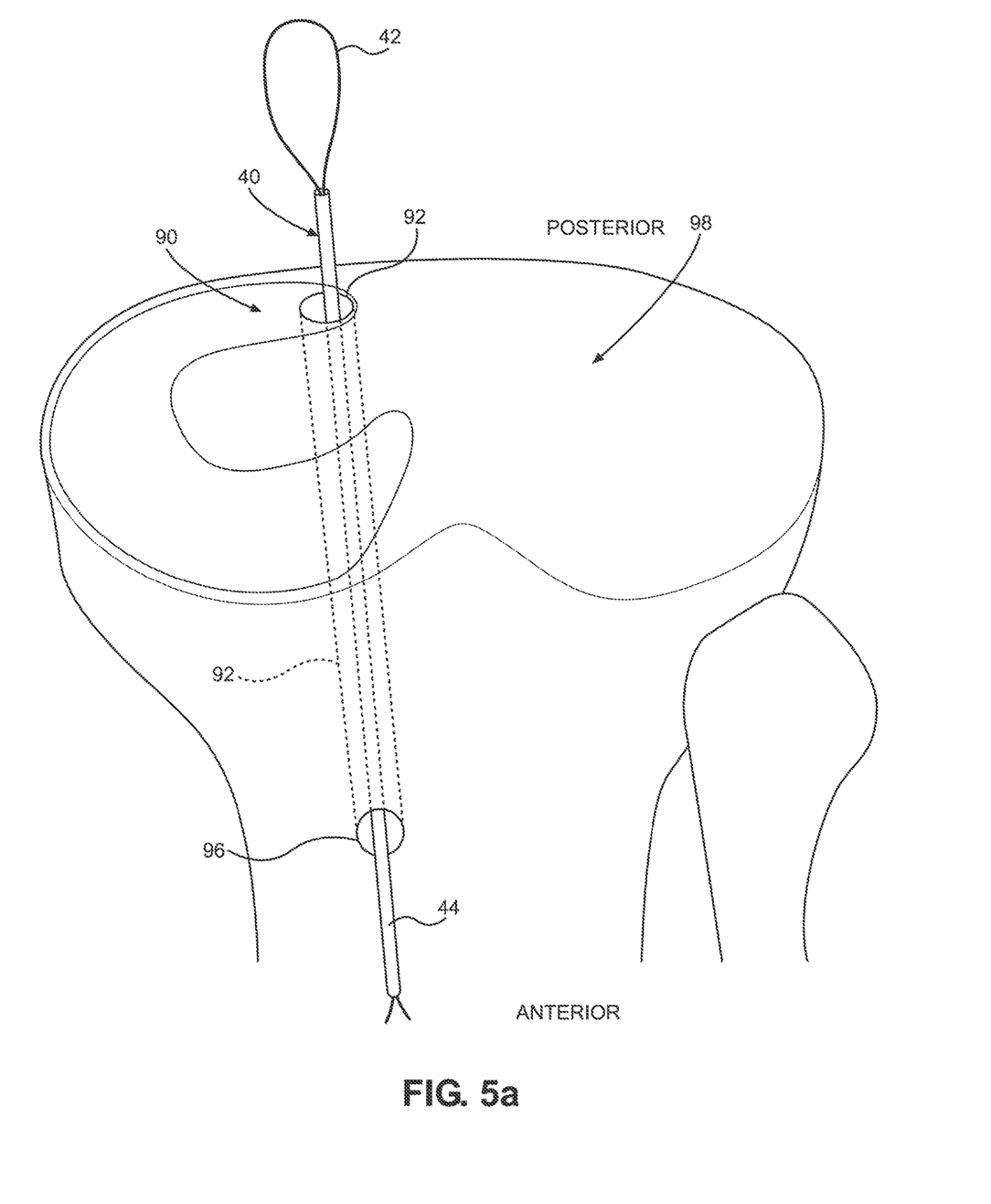

FIGS. 5a-5g illustrate an exemplary method of knotless tissue repair for repair, for example, a meniscus root 90, using the surgical construct 100". Although the surgical construct 100" is shown in the repair method of FIGS. 5a-5g, it will be understood that any of the surgical constructs disclosed herein can be used in the method of FIGS. 5a-5g. Initially, a transtibial bone tunnel 92 is drilled in the tibia bone with an entrance opening 94 thereof at the tibial plateau 98 and an exit opening 96 at the anterior side of the tibia. Once the bone tunnel 92 is prepared, a shuttling device 40, such as a shuttle stitch or the like, is passed through the bone tunnel 92 such that its fixed loop end 42 extends outside of the entrance opening 94 and its opposite distal end 44 extends outside of the exit opening 96, as seen in FIG. 5a.

Figure 5B:
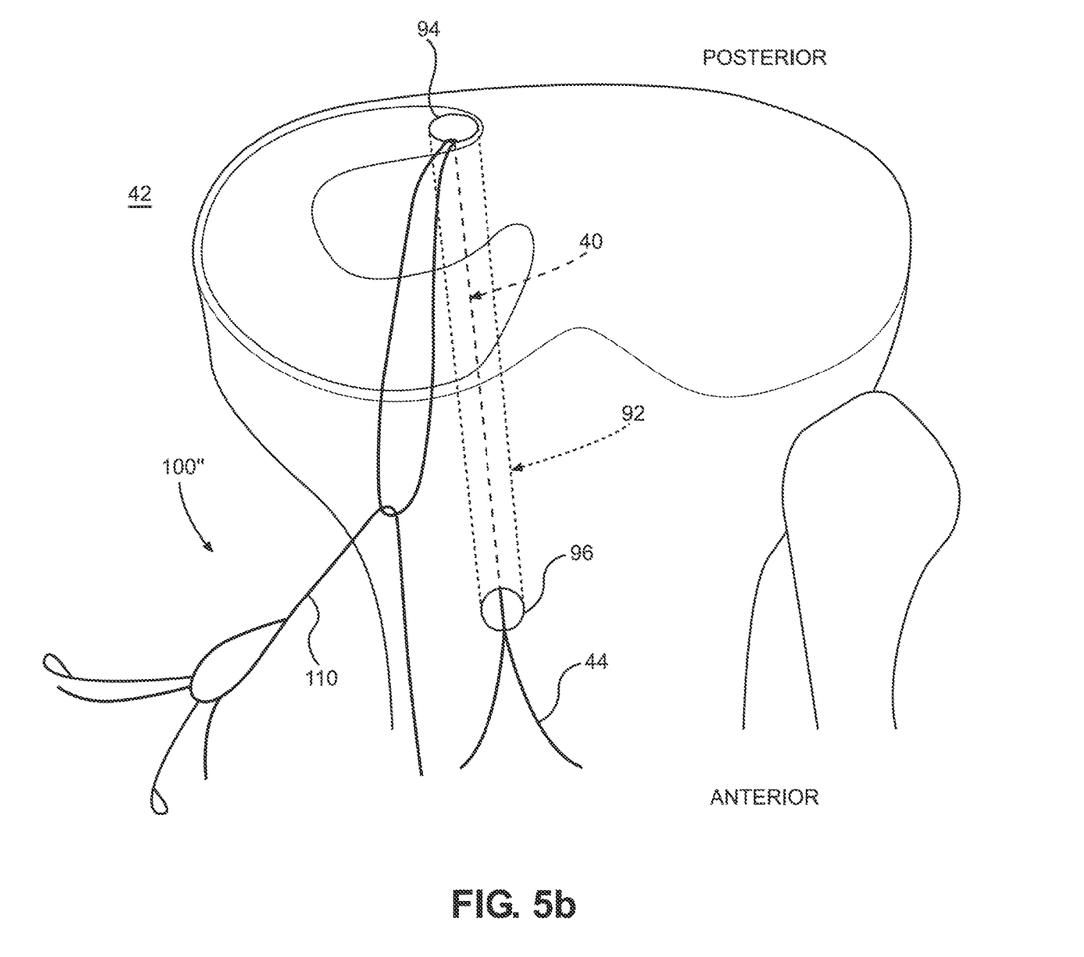

The surgical construct 100" is then loaded onto the shuttling device 40 by extending the fixation device 110 through the fixed loop end 42 of the shuttling device 40, as seen in FIG. 5b. The distal end 44 of the shuttling device 40 is then pulled to lead the surgical construct 100" into the bone tunnel 92 in an antegrade direction, that is from the entrance opening 94 of the tunnel toward the exit opening 96.

Figure 5C:
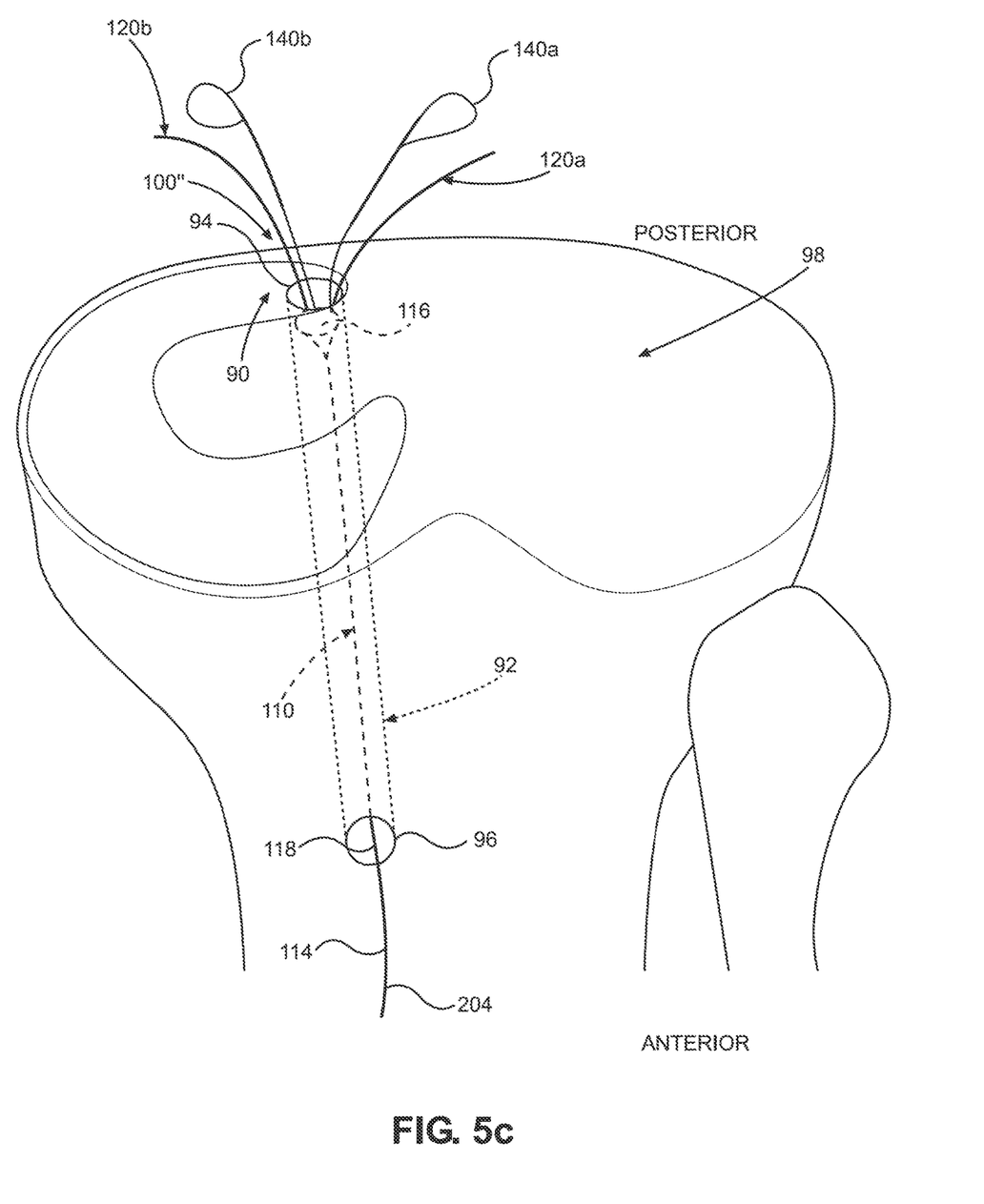
Figure 5D:
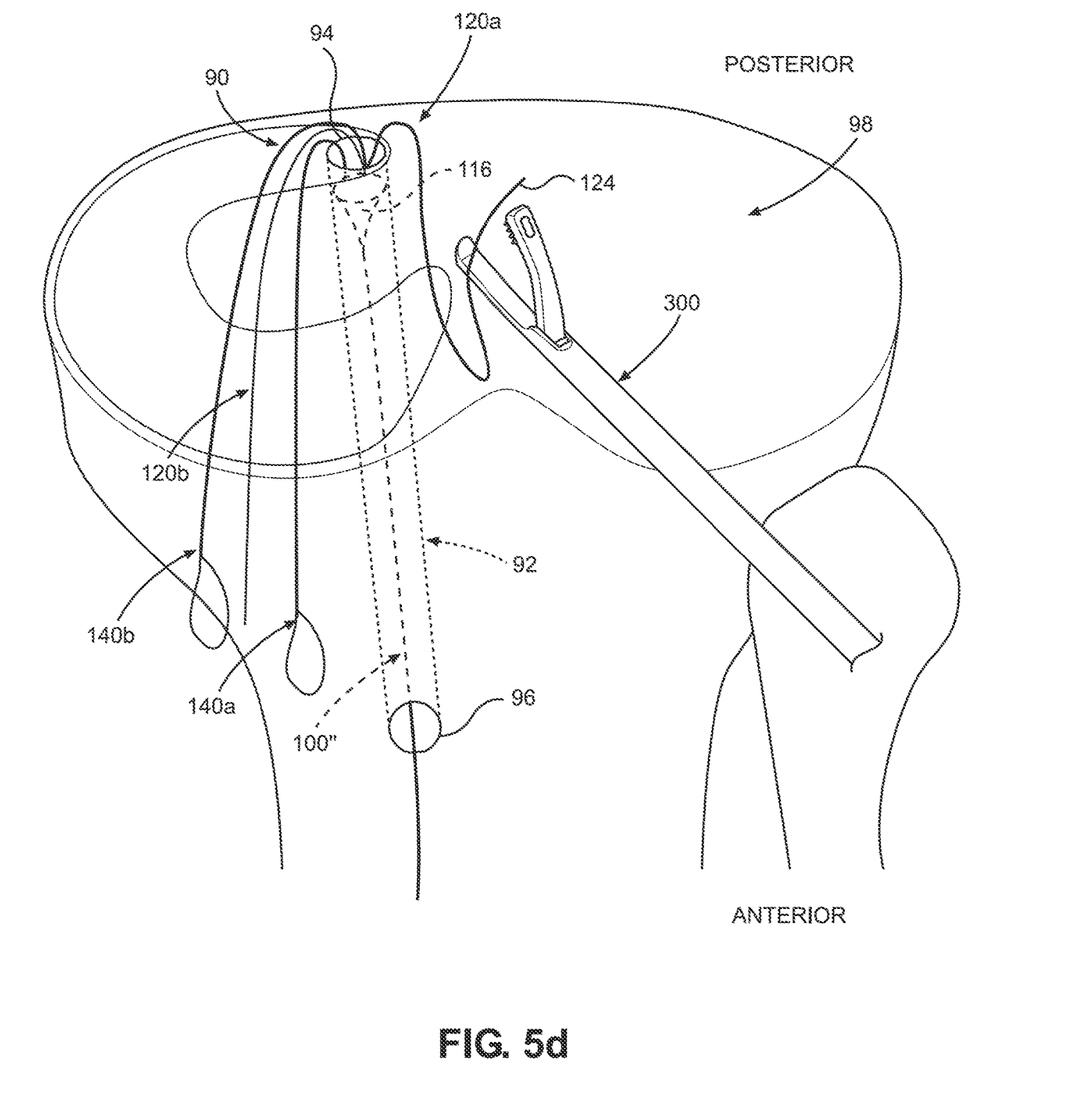

Once the surgical construct 100" has been pulled into the bone tunnel 92 and is properly positioned below the tibial plateau 98, the surgical construct 100" is set or anchored in place in the bone tunnel 92 via the activation member 200 (FIG. 4). In a manner similar to that described above, the distal end 204 of the activation member, which is positioned outside of the exit opening 96 of the bone tunnel, is pulled in the antegrade direction to bunch and compress the head portion 116 of the fixation member 110, as seen in FIG. 5c. The repair strands 120a and 120b and their associated shuttles 140a and 140b remain outside of the bone tunnel 92 at the tibial plateau 98 and available for engaging the meniscus root 90 for the repair thereof. In this set position, the length L (FIG. 4) of the tail portion 118 of the fixation device 110 is long enough such that at least the distal end 114 of the fixation device 110 is outside of the exit opening 96 of the bone tunnel 92.

Once the surgical construct 100" is set in place, the two repair strands 120a and 120b extending from the surgical construct 100" above the tibial plateau 98 are then passed through or around the meniscal root 90. For example, a passing instrument 300 (FIG. 5d), such as the Arthrex Scorpion™, may be used to pass each of the repair strands 120a and 120b through the meniscal root 90.

Figure 5E:
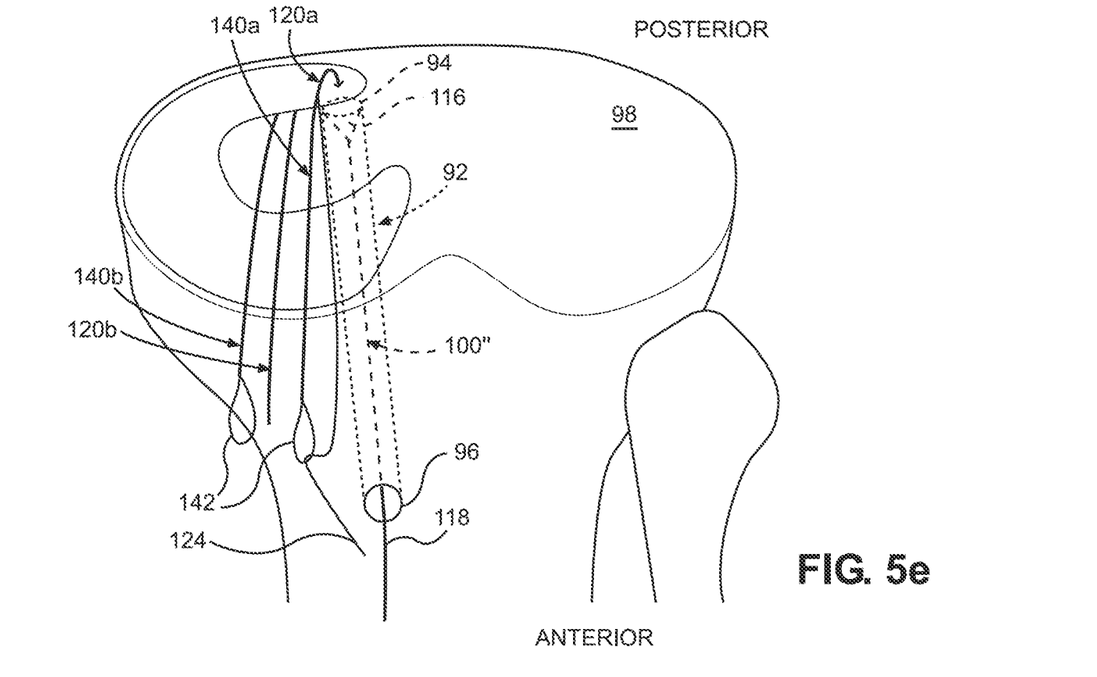
Figure 5F:
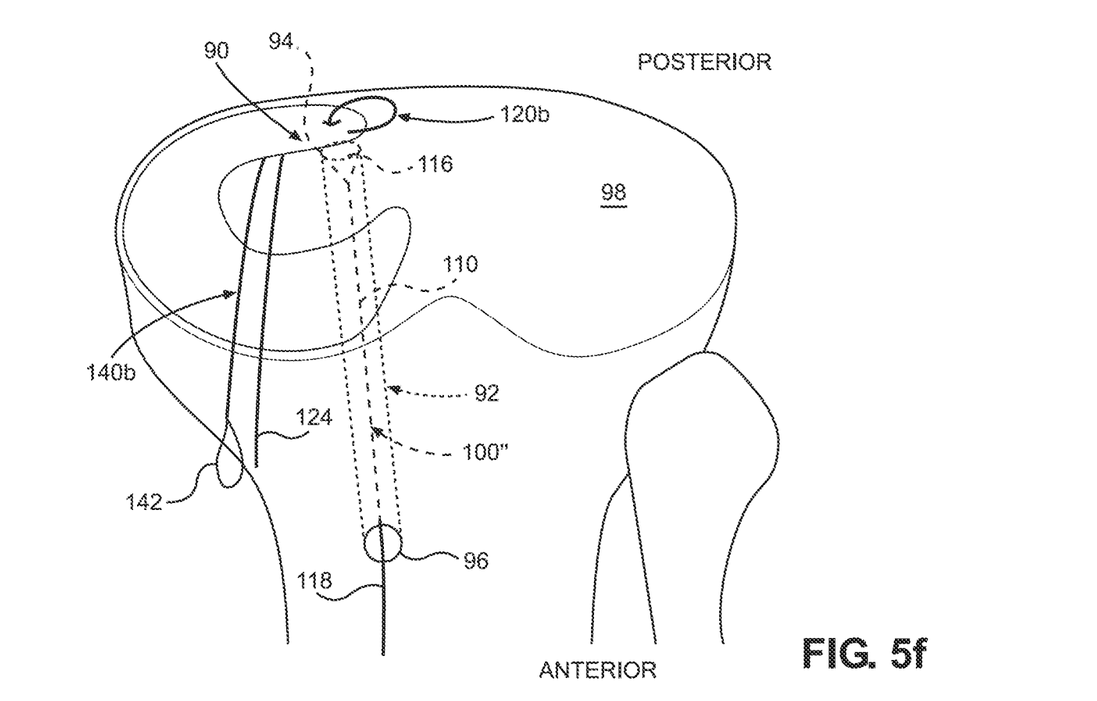
Figure 5G:
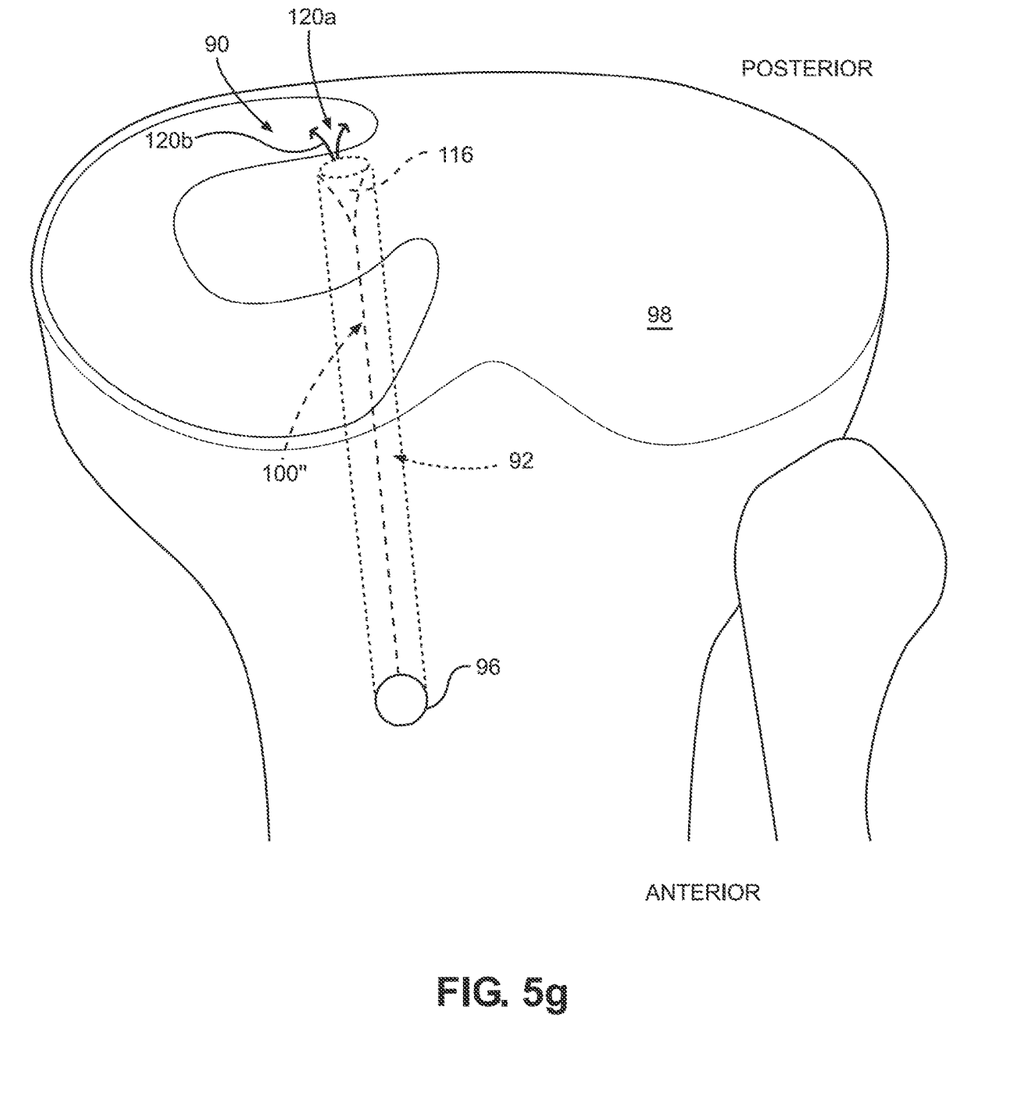

Next, each repair strand 120a and 120b is converted into the surgical construct 100" using their respective shuttles 140a and 140b, as seen in FIGS. 5e and 5f. That is, each repair strand 120a and 120b is pulled in the antegrade direction back through the fixation device 110, including the anchored head portion 116 thereof, in-line with the bone tunnel 92, and out of the exit opening 96 of the bone tunnel 92. The free end 124 of each repair strand 120a and 120b is extended through the fixed loop end 142 of their respective shuttle 140a and 140b, and the distal end 144 (FIG. 4) of their respective shuttle 140a and 140b is then pulled in the antegrade direction through the bone tunnel 92, such that the repair strand free ends 124 are shuttled outside of the exit opening 96 of the bone tunnel. The free ends 124 of the repair strands 120a and 120b are then pulled, or reverse tensioned, to secure the meniscal root 90 down onto the tibial plateau 98 to complete the repair. The portion of the surgical construct 100" remaining outside of the bone tunnel 92 (at its exit opening 96) is then cut flush with the tibia at the anterior side thereof, as seen in FIG. 5g. Advantageously, no additional fixation or fixation device is required for the repair once the repairs strands 120a and 120b are converted and tensioned to tighten the meniscal root 90 to the tibial plateau 98 when completing the repair.

Fixation device 110 of any of the above embodiments can be formed of various soft materials and provided in various shapes and configurations that allow the fixation device 110 to be easily pulled into bone tunnels via its tail portion 118 and its head portion 116 to be bunched up therein. The soft materials of the fixation device 110 may be synthetic or natural materials, or combinations of synthetic and natural materials.

It should be understood that terms such as "lateral," "medial," "distal," "proximal," "superior," and "inferior" are used above consistent with the way those terms are used in the art. Further, these terms have been used herein for purposes of explanation, and should not be considered otherwise limiting. Terms such as "generally," "substantially," and "about" are not intended to be boundaryless terms, and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

What is claimed is:

1. A surgical construct for tissue repair, comprising:
a soft fixation device formed of flexible material, the soft fixation device including a head portion and a tail portion, the head portion forming a loop and the tail portion extending from the loop in an antegrade direction, the device being configured for anchoring the soft fixation device in a bone tunnel, and the tail portion having a length configured to facilitate pulling the soft fixation device in the antegrade direction into the bone tunnel; and
at least one repair flexible strand, the at least one repair flexible strand having at least one free end extending from the head portion in a retrograde direction away from the tail portion, the at least one free end being configured for engaging tissue, and
wherein the flexible material of the loop is a tubular sheath comprising a lumen and the at least one repair flexible strand is configured to be threaded through and inside of the lumen of the tubular sheath.

2. The surgical construct of claim 1, wherein the loop is a closed loop.

3. The surgical construct of claim 1, wherein the loop and the length of the tail portion form one continuous piece.

4. The surgical construct of claim 1, further comprising an activation member coupled to the head portion of the soft fixation device for bunching the head portion.

5. The surgical construct of claim 4, wherein the activation member is at least one flexible strand attached to the head portion of the soft fixation device.

6. The surgical construct of claim 4, wherein the activation member extends through the tail portion of the soft fixation device.

7. The surgical construct of claim 1, further comprising at least one shuttle associated with the at least one repair flexible strand.

8. The surgical construct of claim 7, wherein the at least one shuttle is a flexible strand, a length of the at least one shuttle extends through the tail portion of the soft fixation device.

9. The surgical construct of claim 1, wherein the at least one repair flexible strand comprises a plurality of repair flexible strands that are threaded through and inside of the lumen of the tubular sheath.

10. The surgical construct of claim 1, further comprising a secondary fixation device coupled to the at least one free end of the at least one repair flexible strand.

11. The surgical construct of claim 10, wherein the secondary fixation device is a button.

12. The surgical construct of claim 1, wherein one end of the at least one repair flexible strand has a fixed loop that is configured to receive the free end thereof to form a self-cinching repair.

13. The surgical construct of claim 1, wherein one end of the at least one repair flexible strand has a splice that is configured to receive the free end thereof to form a self-cinching repair.

14. A surgical construct for tissue repair, comprising:
a soft fixation device formed of flexible material, the soft fixation device including a head portion and a tail portion, the head portion being a loop configured for anchoring the soft fixation device in a bone tunnel, and the tail portion having a length that extends from the loop in an antegrade direction and is configured to facilitate pulling the soft fixation device in the antegrade direction into the bone tunnel;
at least one repair flexible strand, the at least one repair flexible strand configured for engaging tissue when repairing the tissue; and
an activation member coupled to the loop of the soft fixation device that is configured to bunch the head portion of the soft fixation device when anchoring the soft fixation device in the bone tunnel, and
wherein the head portion of the flexible material that forms the loop is a tubular sheath that comprises a lumen and the at least one repair flexible strand is configured to be threaded through and inside of the lumen of the tubular sheath.

15. The surgical construct of claim 14, further comprising at least one shuttle associated with the at least one repair flexible strand, the at least one shuttle has a length that extends through the tail portion of the soft fixation device.

16. The surgical construct of claim 15, wherein the at least one repair flexible strand comprises first and second repair flexible strands coupled to the loop of the soft fixation device, and one of the at least one shuttle is associated with each of the first and second repair flexible strands, and each one of the at least one shuttle has a length that extends through the tail portion of the soft fixation device.

17. The surgical construct of claim 16, wherein each of the repair flexible strands, the activation member, and each of the at least one shuttle is a suture or suture tape.

* * * * *